(12) United States Patent
Srinivasan et al.

(10) Patent No.: US 9,739,692 B2
(45) Date of Patent: Aug. 22, 2017

(54) PUMP-LESS METHOD AND APPARATUS FOR SOLVENT EXTRACTION FROM A SAMPLE

(71) Applicant: DIONEX CORPORATION, Sunnyvale, CA (US)

(72) Inventors: Kannan Srinivasan, Tracy, CA (US); S M Rahmat Ullah, Fremont, CA (US)

(73) Assignee: Dionex Corporation, Sunnyvale, CA (US)

( * ) Notice: Subject to any disclaimer, the term of this patent is extended or adjusted under 35 U.S.C. 154(b) by 0 days.

(21) Appl. No.: 14/671,715

(22) Filed: Mar. 27, 2015

(65) Prior Publication Data

US 2016/0282240 A1 Sep. 29, 2016

(51) Int. Cl.
*G01N 31/00* (2006.01)
*G01N 33/00* (2006.01)
*G01N 1/18* (2006.01)
*B01D 21/00* (2006.01)
*G01N 1/34* (2006.01)
(Continued)

(52) U.S. Cl.
CPC ........... *G01N 1/34* (2013.01); *B01D 11/0203* (2013.01); *B01D 11/0207* (2013.01); *B01L 3/52* (2013.01); *B01L 3/561* (2013.01); *B01L 3/567* (2013.01); *B01L 2200/026* (2013.01); *B01L 2200/0631* (2013.01); *B01L 2400/0487* (2013.01); *B01L 2400/06* (2013.01); *B01L 2400/082* (2013.01)

(58) Field of Classification Search
CPC .......... G01N 31/00; G01N 33/00; G01N 1/18; B01D 21/00; B01D 1/02; B01L 99/00; F27B 15/14

USPC .......... 422/81, 527, 530, 543, 146; 436/177, 436/178, 175, 174, 43, 52; 73/1.02, 23.2, 73/19.01, 19.02, 23.41, 23.42, 53.01, 73/61.41, 61.56, 61.59
See application file for complete search history.

(56) References Cited

U.S. PATENT DOCUMENTS

| | | |
|---|---|---|
| 3,062,739 A | 11/1962 | Crits |
| 4,235,715 A | 11/1980 | Wiegert |
| 4,554,132 A * | 11/1985 | Collins .......................... 422/78 |

(Continued)

FOREIGN PATENT DOCUMENTS

| | | |
|---|---|---|
| WO | WO9009233 A1 | 8/1990 |
| WO | WO2004058376 A1 | 7/2004 |
| WO | 2006095093 | 9/2006 |

OTHER PUBLICATIONS

AOAC Official Method 922.06, AOAC Official Methods of Analysis, 1996 AOAC International, 32.1.14.
(Continued)

*Primary Examiner* — Brian J Sines

(57) ABSTRACT

Apparatus for extracting organic analytes from a sample comprising a first compressed gas source connected to valving and a sample extraction cell connected to the valving. A pressure regulator is connected to the extraction cell outlet to the pressure regulator. The pressure regulator blocks fluid flow when the pressure at the pressure regulator inlet is below a predetermined pressure and permits fluid flow when above said predetermined pressure. The apparatus is free of operative association with a mechanical pump or with a compressed gas source other than the compressed gas source. An extraction method for using the above apparatus is described.

2 Claims, 1 Drawing Sheet

(51) Int. Cl.
*B01D 11/02* (2006.01)
*B01L 3/00* (2006.01)

(56) References Cited

U.S. PATENT DOCUMENTS

| | | | | |
|---|---|---|---|---|
| 4,770,780 | A | * | 9/1988 | Moses ............................ 210/634 |
| 4,874,520 | A | | 10/1989 | Lee |
| 5,002,670 | A | | 3/1991 | Pratt |
| 5,087,360 | A | * | 2/1992 | Wright et al. .............. 210/198.2 |
| 5,133,859 | A | * | 7/1992 | Frank et al. ............... 210/198.2 |
| 5,562,963 | A | | 10/1996 | Davis |
| 5,616,407 | A | | 4/1997 | Fritz et al. |
| 5,785,856 | A | | 7/1998 | Gleave et al. |
| 5,843,311 | A | | 12/1998 | Richter et al. |
| 6,087,339 | A | | 7/2000 | Hindsgaul |
| 6,391,204 | B1 | | 5/2002 | Russo, Jr. |
| 6,492,183 | B1 | | 12/2002 | Perman et al. |
| 6,616,893 | B1 | | 9/2003 | Pham |
| 7,981,284 | B2 | * | 7/2011 | Sakamoto et al. ......... 210/198.2 |
| 8,505,806 | B2 | | 8/2013 | Totino et al. |
| 2002/0004535 | A1 | | 1/2002 | Kotsuka et al. |
| 2003/0178370 | A1 | | 9/2003 | Fisk et al. |
| 2009/0035601 | A1 | | 2/2009 | Litton et al. |
| 2011/0133120 | A1 | | 6/2011 | McGhee |
| 2014/0063487 | A1 | * | 3/2014 | Srinivasan et al. .............. 356/51 |

OTHER PUBLICATIONS

AOAC Official method 932.06, AOAC Official Methods of Analysis, 2006 AOAC International, 33.5.08.

AOAC Official Method 989.05, AOAC Official Method of Analysis, 2006 AOAC International, 33.2.26.

Aveldano et al., "Quantitative release of fatty acids from lipids by a simple hydrolysis procedure," J of Lipid Research, 24, 1101-1105, 1983.

Dionex ASE 350 Accelerated Solvent Extractor Operators Manual, Doc. No. 065220, Rev. 04, 268 pages, Dec. 2011.

Hennion, "Solid-phase extraction: method development, sorbents, and coupling with liquid chromatography," J of Chromatography A, 856, 3-54, 1999.

Joshi et al., "Analysis of drugs of abuse from whole human blood," BIOforum Europe, retrieved from internet site: http://www.millipore.com/bibliography.nsf/a73664f9f981af8c852569b9005b4eee/7f7197f9a63c40cf8525722c0052dd8c/$FILE/BioForumEurope1006.pdf, 2006.

Ridgeway et al., "Sample preparation techniques for the determination of trace residues and contaminants in foods," J. of Chromatography A, 1153, 36-53, 2007.

Skoog et al., Analytical Chemistry, An Introduction, Chapter 13, Saunders College Publishing, 6th ed., pp. 227-236.

US EPA Method 3545A, Pressurized Fluid Extraction (PFE), 10 pages, Jan. 1998.

US EPA, National Exposure Research Laboratory, Method 314.0, Determination of perchlorate in drinking water using ion chromatography, 49 pages, Nov. 1999.

Zhou et al., "Development of a hydrothermal deposition process for applying zirconia coatings on BWR materials for IGSCC mitigation," Corrosion Science, 49, 830-843, 2006.

* cited by examiner

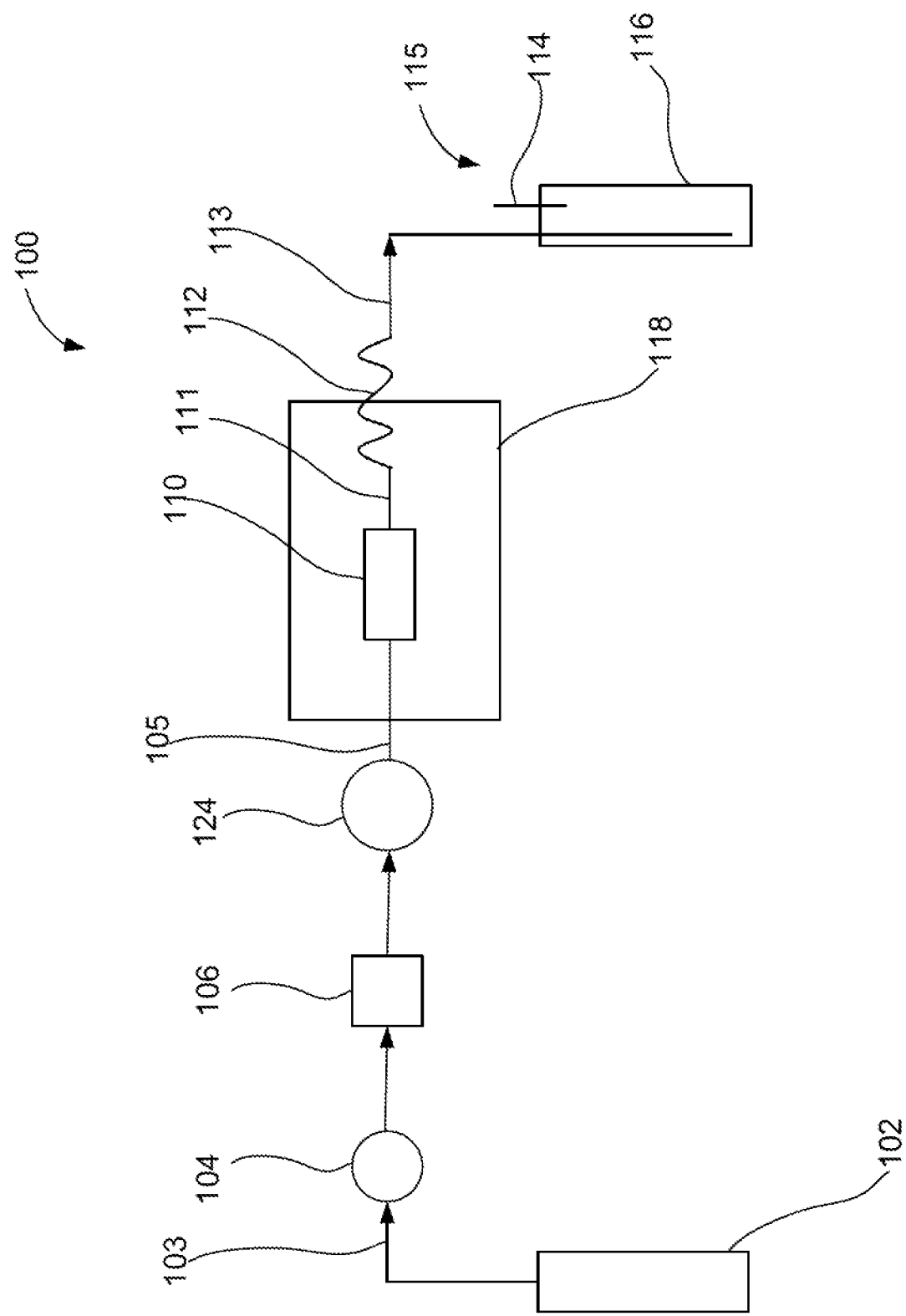

PUMP-LESS METHOD AND APPARATUS FOR SOLVENT EXTRACTION FROM A SAMPLE

FIELD OF THE INVENTION

A method and apparatus for extracting organic analytes from a sample in an organic solvent.

BACKGROUND OF THE INVENTION

U.S. Pat. No. 5,843,311('the 311 patent') describes an analytical method and apparatus for extraction of organic analytes from a sample in a non-aqueous liquid organic solvent in an extraction cell in an oven under elevated temperatures and pressures below supercritical conditions. The method will be referred to as 'accelerated solvent extraction'.

The organic solvent is pumped by a mechanical pump into the extraction cell with an open outlet and then the cell is closed and the system is pressurized under pump pressure. The cell is also heated in the oven to increase the pressure. Alternatively, the cell can be preheated prior to pumping the solvent into the cell. After extraction is complete, a purge gas supplied from a gas tank flows through the cell to displace the solvent containing the extracted analytes which flows to a collection vessel. U.S. Publication No. 2014/0063487 A1 ('the '487 publication'), published Mar. 6, 2014, describes an improved accelerated solvent extraction system. It suggests at paragraph 21 that a compressed gas source may be used to pump the liquid solvent. It describes a restrictor tube 112 which generates back pressure sufficient to maintain the solvent in a liquid state. A commercial embodiment of an accelerated solvent extraction system is sold by Thermo Fisher Scientific under the trademark Dionex 350 Accelerated Solvent Extractor and is described in an Operator's Manual (Document No. 065220, Revision 4, December 2011). It includes a static valve between the extraction cell and collection vessel which opens when a predetermined pressure is exceeded.

These systems are significant improvements over the systems which had been used before them for extracting organic analytes from sample using organic solvents. However, there is a need to reduce the cost of the instruments and methods for performing these extractions and, specifically, to make a portable form of the instrument.

SUMMARY

In one embodiment of the invention, apparatus is provided for extracting organic analytes from a sample. The apparatus includes a first compressed gas source, first valving, a first conduit connecting the compressed gas source with the first valving, a sample extraction cell, and a second conduit connecting the first valving and the sample extraction cell. The first valving has a first position blocking flow from the compressed gas source to the sample extraction cell and a second position permitting fluid flow. The apparatus includes a pressure regulator, and a third conduit connecting the sample extraction cell and pressure regulator. The pressure regulator blocks fluid flow when the pressure at the pressure regulator inlet is below a predetermined pressure and permits fluid flow when the pressure is above the predetermined pressure. A heater is operatively associated with the sample extraction cell. The apparatus is free of operative association with a fourth conduit for liquid solvent connected to said first valving and is free of operative association with a mechanical pump or with a compressed gas source other than the first compressed gas source.

In another embodiment, a method is provided for solvent extraction of organic analytes from a sample. The method includes supplying a sample containing organic analytes and liquid organic solvent to a sample extraction cell having an inlet and an outlet at a pressure less than 50 PSI, starting extraction of the sample organic analytes into the organic solvent in the sample extraction cell at that pressure, and completing extraction under conditions whereby the extraction cell is further pressurized by heating it in the absence of additional pressure supplied by a pressurized fluid flowing to the extraction cell. The extraction cell is maintained under elevated temperature and pressure below supercritical conditions during completion of extraction. The method is performed without the use of a mechanical pump.

BRIEF DESCRIPTION OF THE DRAWINGS

FIG. 1 illustrates one embodiment of an apparatus for performing solvent extraction according to the invention.

DETAILED DESCRIPTION OF EMBODIMENTS

The system of the present invention is useful for extracting a variety of organic analytes using organic solvents such as disclosed in the '311 patent. The embodiment of FIG. 1 is similar to the embodiment of FIG. 1 of the '487 publication, incorporated by reference, with significant deletions. Like parts will be designated by like numbers. FIG. 1 herein illustrates a solid-liquid extraction apparatus 100 designed to extract organic analytes from a sample in a sample extraction vessel (cell) 110. Apparatus 100 may include a compressed gas source 102, a gas valve 104, an optional gas check valve 106, a six-port valve 124, a collection station 115 which includes a collection vessel 116, e.g., a bottle, and an optional gas pressure vent 114. A thermal zone (heater 118), which could be in the form of a water bath in a container around cell 110, can be used to heat cell 110. A first conduit 103 connects compressed gas source 102 and valve 124, also referred to as first valving. A second conduit 105 connects valve 124 and the inlet of extraction cell 110. Valve 124 has a first position blocking flow from compressed gas source 102 to the inlet of cell 110 and a second position permitting fluid flow from source 102 to the inlet of cell 110.

A pressure regulator 112 is disposed between the outlet of cell 110 and the inlet of collection vessel 116. As illustrated, regulator 112 is a restriction tube which performs the function of restriction tube 116 illustrated in FIG. 1 of the '487 publication. A third conduit 111 connects the outlet of cell 110 and pressure regulator 112. All components of the embodiment of FIG. 1 may also be of the type illustrated by like numbers in that publication, incorporated by reference. In one embodiment, pressure regulator 112 blocks or reduces fluid flow when the pressure at the pressure regulator inlet is below a predetermined pressure and permits fluid flow when the pressure at the pressure regulator inlet is above that predetermined pressure. In another embodiment, not shown, the pressure regulator is a static valve which blocks fluid flow completely when the pressure is below the predetermined pressure and opens to permit fluid flow when the pressure is above that predetermined pressure. (This type of regulator is described in the aforementioned Operator's Manual.) A fourth conduit 113 connects pressure regulator 112 and collection bottle 116. After extraction of the analyst into the solvent, remaining solvent in cell 110 can be remove by purging with flow of gas from source 102 through cell 110 by appropriate setting of the valve position of valve 124 or by use a second valve, not shown, in the first valving. "First valving" encompass one or more valves.

In another embodiment, the opening and closing of pressure regulator 112 is time actuated. For example a predetermined time of extraction can be determined empirically for a given application that provides the best recovery results. The static valve could be programmed to open at the predetermined time after the extraction is complete. Another option is to have the opening and closing of the static valve at multiple predetermined times so the extraction proceeds in a batch mode of operation. The flow of solvent can be stopped or started based on the above approach and can provide improved extraction.

In one embodiment, the first valving (valve 124) includes a liquid solvent loop, not shown, whereby a know volume of liquid solvent can be transported from the loop to extraction cell 120 under pressure supplied, preferably solely, by compressed gas source 102. In a specific embodiment, valve 124 supplies such liquid solvent to cell 120 unless blocked in one position of valve 124.

In contrast to the system disclosed in FIG. 1 of the '487 publication, the apparatus of the present invention is free of operative association with a conduit for liquid solvent connected to the first valving (valve 124) other than conduit 103 on the inlet side and conduit 105 on the outlet side. Thus, the apparatus of the invention excludes a conduit connecting the apparatus to a solvent pump 122 illustrated in FIG. 1 of the '487 publication. The present system is also free of operative association with a mechanical pump or a compressed gas source other than source 102. Thus, the liquid solvent can be supplied to a sample loop of valve 124 and then to cell 110 solely under pressure supplied by gas pressure source 102. Also, the solvent containing the analyte may be removed from cell 110 and transported to collection bottle 116 using solely the pressure supplied by source 102. The solvent may be supplied to cell 110 with minimal pressure, e.g. less than 10, 20, 30, 40 or 50 PSI, by pressure from source 102. It also can be supplied under little or no pressure by supplying it independent of gas source 102, as by manual supply. Accurate control of solvent volume can be controlled by using calibrated volumetric glassware for the manual supply option.

The method of solvent extraction of organic analytes from a sample according to the present invention can use the apparatus described above. In a first step, the sample, containing the organic analytes, and liquid organic solvent are supplied the extraction cell. In one embodiment the liquid solvent is added to the cell as a liquid as described above. The solvent may be supplied under the sole pressure of gas supply 102 or supplied manually as by a calibration syringe. In any event, the pressure in cell 110 at the start of extraction need only be sufficient for the supply of the solvent. Thus, at the start of extraction, the cell need not be pressurized sufficiently to perform the extraction. Thus, the pressure in cell 110 at the start of extraction can be less than 10, 20, 30, 40 or 50 PSI. In another embodiment, the solvent is absorbed into a suitable matrix such a DE matrix which is then introduced into cell 110. Here, the pressure at the start of extraction can be ambient pressure.

After introduction of the sample and solvent into cell 110, extraction of the sample analytes can be commenced at the low pressure of introduction. Extraction is completed under conditions whereby the extraction cell is further pressurized by heating in the absence of additional pressure of fluid flowing into the extraction cell. During extraction, the cell is maintained under elevated temperature and pressure below supercritical conditions. Thus, most of the pressure in the cell is supplied by heating of the cell, not by pressurizing the cell by a mechanical pump or gas supplied by a gas pressure source. Suitable maximum pressures for extraction can be less than 200 PSI, preferably less than 100 PSI, and most preferably from 20 to 50 PSI. Such maximum pressures can be the predetermined pressure to open the valve form of pressure regulator to permit flow to collection vessel 116. It should be noted that removing the need for a mechanical pump reduces the expense of the extraction device and method, and increases the portability of the extraction device. The elevated temperature is a temperature value greater than the ambient temperature. The ambient temperature may refer to an environmental temperature that surrounds an external portion of the apparatus when the extraction process is performed. Suitable ambient temperature may range from about 5° C. to about 45° C. The elevated pressure is a pressure value greater than an ambient pressure (e.g., about 14.7 PSI).

In order to illustrate the present invention, the following non-limiting examples of its practice are provided.

EXAMPLE 1

This example describes an apparatus of the type illustrated in the embodiment of FIG. 1 and sample materials which were tested using that device.

Compressed gas source 102 was a nitrogen gas cylinder from Airgas-NCN (Sacramento, Calif.) with an adjustable pressure regulator valve 104. An optional check valve 106 was obtained from Upchurch Scientific/IDEX Corp (CV-3001 and U-469, check valve inline cartridge and cartridge holder, Oak Harbor, Wash.). A 6 port valve 124 (Rheodyne, model 1505, Upchurch Scientific/IDEX Corp, Oak Harbor, Wash.) was connected to the gas stream by using Green PEEK tubing (0.03 inch inner diameter). The purpose of the 6 port valve was to route the gas for the nitrogen gas purge step after the completion of the extraction. In one position, the gas flowed for purging purposes through the sample container. In a second position, the gas flow was blocked and the extraction proceeded. As described above, the gas flow could also be used for other purposes such as loading solvent into the extraction or sample vessel. This can be easily achieved by using an additional 6 port valve to the gas stream. Temperature controller 118 was a water bath (Fisher Scientific, Pittsburg, Pa.) with temperature control. The sample container 110 was a stainless steel sample column (10×150 mm, volume of 11.78 mL, Isolation Technologies, IDEX Health and Science, Middleboro, Mass.). As illustrated in FIG. 1, sample container 110 was placed into a temperature controlled water bath 118. Sample container 110 was connected using stainless steel tubing (0.02 inch I.D.) inside the water bath.

Restriction tube 112 was a stainless steel tube with a 0.02 inch inner diameter×7.87 inch length followed by a red PEEK tubing (0.005 inch inner diameter×10.0 inch length) that was used in between an outlet of sample container 110 and the collection bottle 116. In an alternate embodiment the restrictor tube was replaced by a static valve that opened at a programmed maximum pressure. Collection bottle 116 was obtained from Thermo Scientific Dionex (60 mL, clear collection bottle, P/N 048784).

Various solid food samples were analyzed such as infant formula, cake mix, and parmesan cheese. All reagents used in this work were analytical grade unless specified otherwise. Hexane, ACS grade (Sigma-Aldrich, St. Louis, Mo., USA), dichloromethane, ACS grade (Sigma-Aldrich, St.

Louis, Mo., USA), methanol HPLC grade (Honeywell Burdick and Jackson, Muskegon, Mich.), and isopropanol (General Chemicals, Parsippany, N.J.) were used as extraction solvents. The infant formula sample was Similac® Advance® infant formula and was obtained from Abbot Laboratories (Columbus, Ohio). The cake mix was a Pillsbury® cake mix from Pillsbury Company (Minneapolis, Minn.). The parmesan cheese sample was from Kraft Foods (Northfield, Ill.). The diatomaceous earth absorbent (ASE Prep DE) was from Thermo Scientific Dionex (Sunnyvale, Calif.).

EXAMPLE 2

Example 2 shows the experimental procedure and steps using the system of the present invention.

ASE™ Prep DE was ground using a mortar and pestle and weighed (0.6 g-1.2 g). Next, a food sample from above (app. 0.6-1.2 g) was placed into a weighing pan and measured to the nearest 0.0001 grams. The weight ratio of ground DE to solid sample was typically at a ratio of about 1:1 or slightly higher (e.g., 2:1). The solid food sample was also placed into the mortar from above and ground thoroughly by a pestle. The water bath 118 was set to 100° C. The six port valve was switched so that the gas flow was blocked.

The sample container was assembled by first placing a bottom frit and the end cap. The mixture of the ground DE and solid food sample was added to the container. The bottom part of the cell was connected to the collection bottle. Solvent was poured into the sample cell. Next, a top end cap with a frit was assembled to complete the assembly of sample container 110. The top end of the sample cell 110 was connected upstream with the 6 port valve 124 to complete the set-up. The sample cell 110 was then immersed in the water bath 118 for extraction. The analytes dissolved in the solvent and flowed slowly into the collection bottle. When the extraction time was complete the six port valve was switched to allow a nitrogen gas purge that pushed any residual solvent into the collection bottle. The liquid solvent containing the dissolved sample was collected in a 60 mL collection bottle and evaporated to dryness. The amount of lipids collected from the food samples were determined gravimetrically by comparing the weight of the collection bottle before (dry and clean container) and after extraction (after solvent evaporation). The result was compared to the fat content listed in the product label.

EXAMPLE 3

This example illustrates the utility of the extraction system of the present invention using the apparatus of Example 1. The general procedure was similar to Example 2. The solid sample was an infant formula sample. The weight ratio of ground DE to solid sample in this example was 1:1. The sample weight was 1 g. The duration of the extraction was set to 20 minutes. The extraction solvent was hexane, dichloromethane, and methanol in a 5:2:1 volume ratio. A nitrogen gas purge (60 psi for 2 minutes) was invoked at the end of the extraction by switching the 6 port valve. Table 1 shows the lipid recovery percentage, the volume of liquid solvent added and the volume of liquid solvent collected.

TABLE 1

| Solvent Added Pre Extraction, mL | Lipid Recovery, % | Solvent Collected Post Extraction, mL |
| --- | --- | --- |
| 8.50 | 101.1 | 7.45 |

Excellent recovery using the present extraction method was evident from the observed recovery of 101.1%. A standard ASE setup using a pump also provided a similar recovery. The small reduction in the collected solvent was from evaporation of the solvent during the extraction/collection period.

EXAMPLE 4

This example illustrates the utility of the extraction system of the present invention using the apparatus of Example 1. The general procedure was similar to Example 2. The sample in this case was a solid cake mix sample. The weight ratio of ground DE to solid sample in this example was 1:1. The sample weight was 1 g. The duration of the extraction was 20 minutes. The extraction solvent was hexane, dichloromethane, and methanol in a 5:2:1 volume ratio. A nitrogen gas purge (60 psi for 2 minutes) was invoked at the end of the extraction by switching the 6 port valve. Table 2 shows the lipid recovery percentage, the volume of liquid solvent added and the volume of liquid solvent collected.

TABLE 2

| Solvent Added Pre Extraction, mL | Lipid Recovery, % | Solvent Collected Post Extraction, mL |
| --- | --- | --- |
| 8.50 | 99.87 | 7.04 |

Excellent recovery using the present extraction method was evident from the observed recovery of 99.87%. A standard ASE setup using a pump also provided a similar recovery. The small reduction in the collected solvent was from evaporation of the solvent during the extraction/collection period.

EXAMPLE 5

This example illustrates the utility of the extraction system of the present invention using the apparatus of Example 1. The general procedure was similar to Example 2. The sample in this case was a parmesan cheese. The weight ratio of ground DE to solid sample in this example was 2:1. The sample weight was 0.6 g. The duration of the extraction was 20 minutes. The extraction solvent was hexane, dichloromethane, and methanol in a 5:2:1 volume ratio. A nitrogen purge (60 psi for 2 minutes) was invoked at the end of the extraction by switching the 6 port valve. Table 3 shows the lipid recovery percentage, the volume of liquid solvent added and the volume of liquid solvent collected.

TABLE 3

| Solvent Added Pre Extraction, mL | Lipid Recovery, % | Solvent Collected Post Extraction, mL |
| --- | --- | --- |
| 9.00 | 100.8 | 8.53 |

Excellent recovery using the present extraction method was evident from the observed recovery of 100.8%. A standard ASE setup using a pump also provided a similar recovery. The small reduction in the collected solvent was from evaporation of the solvent during the extraction/collection period.

What is claimed is:
1. An apparatus for extracting organic analytes from a sample, said apparatus comprising,
(a) a compressed gas source,
(b) first valving,

(c) a first conduit connecting said compressed gas source with said first valving, (d) a sample extraction cell having an inlet and an outlet, (e) a second conduit connecting said first valving and said sample extraction cell inlet, said first valving having a first position blocking flow from said compressed gas source to said sample extraction cell inlet and a second position permitting fluid flow from said compressed gas source to said sample extraction cell inlet, (f) a pressure regulator having an inlet and an outlet, (g) a third conduit connecting said sample extraction cell outlet and said pressure regulator, said pressure regulator blocking fluid flow when the pressure at said pressure regulator inlet is below a predetermined pressure and permitting fluid flow when said pressure at said pressure regulator inlet is above said predetermined pressure, and (h) a heater operatively associated with said sample extraction cell, wherein said apparatus does not include another conduit that i) provides fluid communication between a source of liquid solvent and the sample extraction cell and ii) is fluidically coupled to a mechanical pump; and wherein said apparatus does not include another conduit that i) provides fluid communication between a source of liquid solvent and the sample extraction cell and ii) is fluidically connected to any compressed gas source including said first compressed gas source.

2. The apparatus of claim 1 further comprising, (i) a collection station for collecting organic sample analytes extracted into a liquid solvent in said sample extraction cell, and (j) a fourth conduit connecting said pressure regulator and said collection station.

* * * * *